United States Patent
Ellis et al.

(10) Patent No.: US 6,828,328 B1
(45) Date of Patent: Dec. 7, 2004

(54) ANALGESIC COMBINATION OF MUSCARINIC AGONISTS

(75) Inventors: James Ellis, Boxford, MA (US); Fangming Zou, Wilmington, MA (US)

(73) Assignee: UCB s.A., Brussels (BE)

(*) Notice: Subject to any disclaimer, the term of this patent is extended or adjusted under 35 U.S.C. 154(b) by 0 days.

(21) Appl. No.: 10/087,283

(22) Filed: Mar. 1, 2002

(51) Int. Cl.[7] ................ A61K 31/44; A61K 31/415; A61K 31/19; A61K 31/16; A61K 31/34
(52) U.S. Cl. ............... 514/294; 514/282; 514/629; 514/570; 514/406; 514/473
(58) Field of Search ................ 514/294, 282, 514/629, 570, 406, 473

(56) References Cited

U.S. PATENT DOCUMENTS 6,093,724 A * 7/2000 Grewal et al. .............. 514/294

* cited by examiner

*Primary Examiner*—Shengjun Wang
(74) *Attorney, Agent, or Firm*—McDonnell Boehnen Hulbert & Berghoff LLP

(57) ABSTRACT

This invention relates to the combination of muscarinic agonists with narcotic analgesics, non-steroidal anti-inflammatory drugs or other analgesic drugs and to their use as antinociception (pain relief) agents. In particular, the invention relates to a combination of a specific class of M4 selective muscarinic agonists with narcotic analgesics, non-steroidal anti-inflammatory drugs or other analgesic drugs.

5 Claims, No Drawings

ANALGESIC COMBINATION OF MUSCARINIC AGONISTS

This invention relates to the combination of muscarinic agonists with narcotic analgesics, non-steroidal anti-inflammatory drugs or other analgesic drugs and to their use as antinociception (pain relief) agents. In particular, the invention relates to a combination of a specific class of M4 selective muscarinic agonists with narcotic analgesics, non-steroidal anti-inflammatory drugs or other analgesic drugs.

Both narcotic analgesics (e.g. morphine) and non-steroidal anti-inflammatory drugs (NSAIDs) are well-known analgesics. Use of narcotic analgesics is limited by their ability to produce tolerance and addiction and their side effect profile. Side effects of narcotic analgesics include constipation, respiratory depression and nausea. NSAIDs are generally well tolerated but less efficacious analgesic agents.

Muscarinic agents have been shown to be effective analgesic agents in animal models with an efficacy similar to morphine but with much greater potency. The concept of using muscarinic agonists as potential analgesic agents for use in humans has been around for about five decades. Despite this there have been no muscarinic agonists approved for the treatment of pain. The primary reason for this has been their unacceptable side effect profile. A lack of understanding of the muscarinic receptor subtype mediating antinociception versus the side effects has further hampered work in this area. Recently however it has been shown that agonists which act selectively at the M4 receptor may provide good antinociception with an improved side effect profile (Ellis et al., The Journal of Pharmacology and Experimental Therapeutics, 288(3), 1999).

A class of M4 selective muscarinic agonists with reduced cholinergic side effects is described in WO 00/11001. These compounds are members of classes of azaadamantanes, azanoradamantanes and azahomoadamantanes.

Despite the work done in this field there remains a need for anti-nociceptive compositions having an improved analgesic profile without increasing side effects.

The present invention brings a solution in that it has now been found that a class of M4 selective muscarinic agonists when used in combination with additional analgesics enables an analgesic effect to be reached with concomitant reduction of undesirable side-effects compared to those side-effects experienced when either the M4 selective muscarinic agonists or the additional analgesics are administered alone in a concentration able of reaching the same analgesic effect. The additional analgesics may be narcotic analgesics, non-steroidal anti-inflammatory drugs (NSAID's) or other analgesics. In particular embodiments, the class of M4 selective muscarinic agonists when used in combination with narcotic analgesics, non-steroidal anti-inflammatory drugs (NSAID's) or other analgesics produces synergism or super-additivity in the analgesic profile without increasing side effect liabilities.

The present invention relates thus to a composition comprising at least one M4 selective muscarinic agonist selected from the azacyclic ring system having the formula I

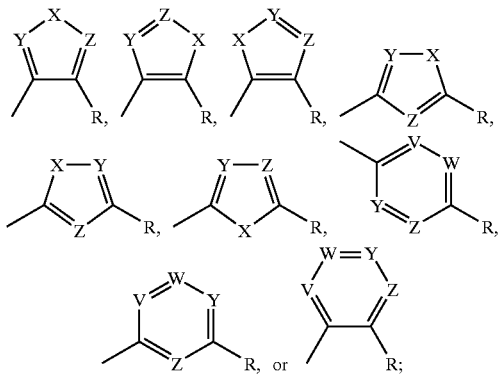

including geometrical isomers, enantiomers, diastereomers, racemates, acid addition salts, salts thereof with a pharmaceutically acceptable acid, and prodrugs thereof, wherein Q is X is —$CH_2$—, —NH—, —O— or —S—;
V, W, Y and Z independently are CH or N;
n and m independently are 0, 1, 2, 3 or 4;
$R^1$ and $R^2$ are at any position on the azacyclic ring, including the point of attachment of the heterocycle Q, and independently are hydrogen, —OH, halogen, —$NH_2$, carboxy, straight or branched $C_{1-10}$-alkyl, $C_{1-10}$-alkenyl, or $C_{1-10}$-alkynyl, straight or branched $C_{1-10}$-alkoxy, or straight or branched $C_{1-10}$-alkyl substituted with —OH, —CN, —CHO, —OH, —$OR^3$, —$SR^3$, —$NH_2$, —NHR, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CH=$NOR^3$; or
$R^1$ and $R^2$ independently are phenyl, phenoxy, benzoyl, benzyl or benzyloxycarbonyl, each of which are unsubstituted or substituted with halogen, —CN, $C_{1-10}$-alkyl, $C_{1-10}$-alkoxy, or $C_{1-10}$-alkylthio;
R is hydrogen, halogen, —CN, —CHO, —OH, —$OR^3$, —$SR^3$, —$NH_2$, —$NHR^3$, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CN=$NOR^3$; or
R is phenyl, phenoxy, benzoyl, benzyl or benzyloxycarbonyl, each of which are unsubstituted or substituted with halogen, —CN, $C_{1-15}$-alkyl, $C_{1-10}$-alkoxy, or $C_{1-10}$-alkylthio; or
R is a 5 or 6 membered saturated, partly saturated or aromatic heterocyclic ring containing one to three heteroatoms; and
$R^3$ and $R^4$ independently are straight, branched, or cyclic $C_{1-15}$-alkyl, $C_{2-15}$-alkenyl, $C_{2-15}$-alkynyl, or combinations thereof, or $R^3$ and $R^4$ independently are phenyl, phenoxy, benzoyl, benzyl or benzyloxycarbonyl groups, each of which are unsubstituted or substituted with H, halogen, —CN, $C_{1-15}$-alkyl, $C_{1-10}$-alkoxy, $C_{1-10}$-alkylthio, or aryl; or
$R^3$ and $R^4$ independently are 5 or 6 membered saturated, partly saturated or aromatic heterocyclic rings containing one to three heteroatoms; and
further comprising one or more additional analgesics.

In preferred embodiments, the one or more additional analgesics produce a synergistic or super-additive effect ("synergistic analgesics or super-additive").

In a preferred embodiment, the present invention relates to a composition as defined above wherein in formula I of the M4 selective muscarinic agonist n and m both are 1 and the azayclic ring system has the structural formula:

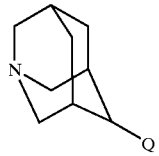

II wherein

Q is:

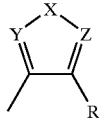

X is S,

Y and Z are N, and

R is $OR^3$ or $SR^3$.

In a more preferred embodiment, the present invention relates to a composition as defined above wherein $R^3$ of the M4 selective muscarinic agonist is —$CH_3$, —$CH_2CH_3$, —$CH_2CH_2CH_3$ or —$CH_2CH(CH_3)_2$.

In a still more preferred embodiment, the invention relates to a composition comprising at least one M4 selective muscarinic agonist selected from the group consisting of, 3-(5-Aza-2-chlorotricyclo[3.3.1.1<3,7>]dec-2-yl)-4-chloro-1,2,5-thiadiazole, 3-(5-Azatricyclo-[3.3.1.1<3,7>]dec-2-yl)-4-chloro-1,2,5-thiadiazole, 3-(5-azatricyclo[3.3.1.1<3,7>]dec-2-yl)-4-methoxy-1,2,5-thiadiazole, 3-(5-azatricyclo-[3.3.1.1<3,7>]dec-2-yl)-4-ethoxy-1,2,5-thiadiazole, 3-(5-azatricyclo[3.3.1.1<3,7>]dec-2-yl)-4-propoxy-1,2,5-thiadiazole, 3-(5-azatricyclo[3.3.1.1<3,7>]dec-2-yl)-4-butoxy-1,2,5-thia-diazole, 3-(5-azatricyclo-[3.3.1.1<3,7>]dec-2-yl)-4-(cyclopropylmethoxy)1,2,5-thiadiazole, 3-(5-azatricyclo-[3.3.1.1<3,7>]dec-2-yl)-4-(2-methyl-propoxy)-1,2,5-thiadiazole, 4-[4-(propylsulfanyl)-1,2,5-thiadiazol-3-yl]-1-azatricyclo[3.3.1.1<3,7>]decane, 4-[4-(methylsulfanyl)-1,2,5-thiadiazol-3-yl]-1-azatricyclo[3.3.1.1<3,7>]decane, 4-[4-(ethylsulfanyl)-1,2,5-thiadiazol-3-yl]-1-azatricyclo[3.3.1.1<3,7>]decane, 4-[4-(butylsulfanyl)-1,2,5-thiadiazol-3-yl]-1-azatricyclo-[3.3.1.1<3,7>]decane, 4-[4-(2-methyl-propylsulfanyl)-1,2,5-thiadiazol-3-yl]-1-azatricyclo-[3.3.1.1<3,7>]decane, 4-[4-(cyclopropylmethylsulfanyl)-1,2,5-thiadiazol-3-yl]-1-azatricyclo-[3.3.1.1<3,7>]decane and further comprising one or more additional analgesics.

In a most preferred embodiment, the invention relates to a composition comprising the M4 selective muscarinic agonist 4-s-[4-(propylsulfanyl)-1,2,5-thiadiazol-3-yl]-1-azatricyclo[3.3.1.1<3,7>]decane and further comprising one or more additional analgesics.

In a further preferred embodiment of the invention, the compositions further comprise a pharmaceutically acceptable carrier.

In another embodiment, the invention relates to a method of inducing analgesia, the method comprising co-administration of at least one M4 selective muscarinic agonist selected from the azacyclic ring system having the formula I

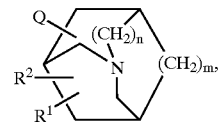

I including geometrical isomers, enantiomers, diastereomers, racemates, acid addition salts, salts thereof with a pharmaceutically acceptable acid, and prodrugs thereof, wherein Q is

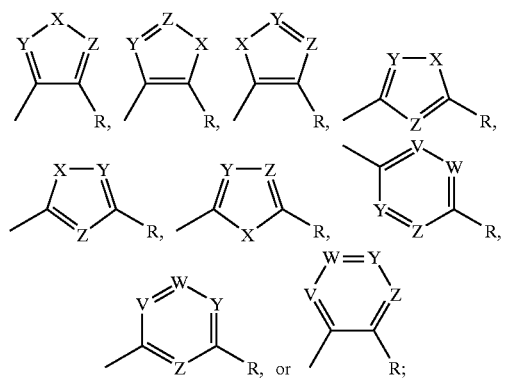

X is —$CH_2$—, —NH—, —O— or —S—;

V, W, Y and Z independently are CH or N;

n and m independently are 0, 1, 2, 3 or 4;

$R^1$ and $R^2$ are at any position on the azacyclic ring, including the point of attachment of the heterocycle Q, and independently are hydrogen, —OH, halogen, —$NH_2$, carboxy, straight or branched $C_{1-10}$-alkyl, $C_{1-10}$-alkenyl, or $C_{1-10}$-alkynyl, straight or branched $C_{1-10}$-alkoxy, or straight or branched $C_{1-10}$-alkyl substituted with —OH, —CN, —CHO, —OH, —$OR^3$, —$SR^3$, —$NH_2$, —$NHR^3$, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CN=$NOR^3$; or $R^1$ and $R^2$ independently are phenyl, phenoxy, benzoyl, benzyl or benzyloxycarbonyl, each of which are unsubstituted or substituted with halogen, —CN, $C_{1-10}$-alkyl, $C_{1-10}$-alkoxy, or $C_{1-10}$-alkylthio;

R is hydrogen, halogen, —CN, —CHO, —OH, —$OR^3$, —$SR^3$, —$NH_2$, —$NHR^3$, —$NR^3R^4$, —$NO_2$, —$SOR^3$, —$SO_2R^3$, —$COR^3$, —$CO_2R^3$, —$CONH_2$, —$CONHR^3$, —$CONR^3R^4$, or —CN=$NOR^3$; or R is phenyl, phenoxy, benzoyl, benzyl or benzyloxycarbonyl, each of which are unsubstituted or substituted with halogen, —CN, $C_{1-15}$-alkyl, $C_{1-10}$-alkoxy, or $C_{1-10}$-alkylthio; or R is a 5 or 6 membered saturated, partly saturated or aromatic heterocyclic ring containing one to three heteroatoms; and $R^3$ and $R^4$ independently are straight, branched, or cyclic $C_{1-15}$-alkyl, $C_{2-15}$-alkenyl, $C_{2-15}$-alkynyl, or combinations thereof, or $R^3$ and $R^4$ independently are phenyl, phenoxy, benzoyl, benzyl or benzyloxycarbonyl groups, each of which are unsubstituted or substituted with H, halogen, —CN, $C_{1-15}$-alkyl, $C_{1-10}$-alkoxy, $C_{1-10}$-alkylthio, or aryl; or R³ and R⁴ independently are 5 or 6 membered saturated, partly saturated or aromatic heterocyclic rings containing one to three heteroatoms; with one or more additional analgesics.

The term "co-administration" relates both to simultaneous administration and to immediate subsequent administration of at least one M4 selective muscarinic agonist and one or more additional analgesics. In the case of simultaneous administration, the at least one M4 selective muscarinic agonist and the one or more additional analgesics may be administered individually or in the form of a fixed combination, as described in the above sections.

Thus, in a particular embodiment, the invention relates to a method of inducing analgesia, the method comprising administering an analgesia-inducing amount of a composition as defined in the above sections to a mammal in need thereof.

The invention also relates to a composition as defined above for use as a medicament, preferably for use as an analgesic.

In a further embodiment the invention relates to the use of a composition as defined above for the manufacture of a medicament for the treatment of analgesia.

The term aryl as used herein refers to phenyl, substituted phenyl, or heteroaryl (as further defined below) wherein the substituent is halo, alkyl, alkoxy, alkylthio, haloalkyl, hydroxyalkyl, alkoxyalkyl, methylenedioxy, cyano, C(O) alkyl, carboxy, C(O)₂alkyl, amide, amino, alkylamino and dialkylamino, and wherein the aryl group can have up to 3 substituents.

The term halo, as used herein, includes fluoro, chloro, bromo, and iodo.

The term heteroatom refers to N, S, or O.

The term heterocycle means a cycloalkyl moiety substituted in the ring by one or more heteroatoms.

The term heteroaryl and heteroaromatic, as used herein, refers to an aromatic moiety that includes at least one heteroatom in the aromatic ring.

The term M4 selective muscarinic agonists refers to agonists that have high affinity and agonist activity at the M4 receptor subtype but have low or very low agonist activity at the other muscarinic receptors subtypes M1, M2, M3 and M5. The M4 selective muscarinic agonists having the formula I according to the invention have a good therapeutic index, which is the ratio between desirable analgesic effects versus side effects.

The term synergistic or super-additive analgesic refers to any analgesics which in combination with the M4 selective muscarinic agonists having the formula I lead to potentiated pain relief without increasing side effect liabilities. The term is intended to include opioid analgesics, nonsteroidal anti-inflammatory agents (NSAIDs) and other analgesics.

The term opioid analgesic, as used herein, represents opioids and opioid antagonists. The term opioid represents natural or synthetic substances, that bind to opiate receptors and produce an agonist action.

The term opioid antagonist refers to opioid-like substances that bind to opiate receptors but produce little or no agonist activity. These substances are also effective pain relievers. The term opioid analgesic includes morphine, codeine, dihydrocodeine, meptazinol, dezocine, cyclazocine, tramadol, meperidine, methadone, propoxyphene, levorphanol, hydromorphone, hydrocodone, oxymorphone, oxycodone, pentazocine, naloxone, nalorphine, naltrexone, butorphanol, nalbuphine and buprenorphine but is not limited thereto.

Preferred opioid analgesics are selected from morphine and codeine. The most preferred opioid analgesic is morphine.

The term nonsteroidal anti-inflammatory drugs (NSAIDs) refers to a heterogeneous group of drugs that are useful in the symptomatic treatment of inflammation and that have analgesic properties. It includes acetaminophen, the non-selective COX inhibitors such as aspirin, ibuprofen, indomethacin, diclofenac, diflusinal, etodolac, fenbufen, fenoprofen, flufenisal, flurbiprofen, ketoprofen, ketorolac, meclofenamic acid, mefenarnic acid, nabumetone, naproxen, oxaprozin, phenylbutazone piroxicam, sulindac, tolmetin, zomepirac and the selective COX-2 inhibitors such as NS-398, celecoxib and rofecoxib but is not limited thereto. Preferred nonsteroidal anti-inflammatory drugs are acetaminophen, ibuprofen, celoxicib and refoxicib.

The term other analgesics includes nicotinic agonists such as ABT-594, NMDA (N-methyl-D-aspartate) antagonists such as dextromethorphan, dextrorphan, amantadine, memantine, anti-epileptics such as gabapentin, levetiracetam, pregabalin and alpha adrenoceptor agonists such as clonidine but is not limited thereto.

The present invention is illustrated by the following examples.

A. 4s-[4-(propylsulfanyl)-1,2,5-thiadiazol-3-yl]-1-azatricyclo[3.3.1.1<3,7>]decane hydrochloride in Combination with Morphine in the Mouse Tail-flick Test 4-s-[4-(propylsulfanyl)-1,2,5-thiadiazol-3-yl]-1-azatricyclo[3.3.1.1<3,7>]decane hydrochloride is a functionally selective M4 muscarinic agonist analgesic. Its antinociception (analgesia) in vivo had been investigated using the mouse tail flick test. The mouse tail-flick test is a well-known experimental model to verify the analgesic activity of potential moderate and severe pain relievers including muscarinic agonists (Chau, T. T: Analgesic Testing in Animal Models. Pharmacological Methods in the Control of Inflammation. 195–212. 1989, Alan R. Liss. Inc.). In this series of mouse tail-flick test experiments, 4-s-[4-(propylsulfanyl)-1,2,5-thiadiazol-3-yl]-1-azatricyclo [3.3.1.1<3,7>]decane hydrochloride was tested in combination with morphine sulfate, an opiate agent that is a widely used analgesic in medical practice. Other possible muscarinic agonist activities, such as tremor, sedation, salivation, and hypothermia were observed simultaneously.

1. Materials and Methods

Test Substances

4s-[4-(propylsulfanyl)-1,2,5-thiadiazol-3-yl]-1-azatricyclo[3.3.1.1<3,7>]decane hydrochloride was dissolved in normal physiological saline (0.9% NaCl solution) for sc administration. The final dosing solution of 4-s-[4-(propylsulfanyl)-1,2,5-thiadiazol-3-yl]-1-azatricyclo [3.3.1.1<3,7>]decane hydrochloride was prepared so that the appropriate dose (0.003–0.05 mg/kg) was achieved with 10 ml/kg (body weight) of injected test compound solution.

Morphine (morphine sulfate, M-8777) was purchased from Sigma Chemical Co. (St. Louis, Mo., USA) and dissolved in normal physiological saline (0.9% NaCl solution) for subcutaneous injection (sc). The final dosing solution of morphine was prepared so that the appropriate dose (3.0–5.0 mg/kg) was achieved with 10 ml/kg (body weight) of injected test compound solution.

Animals

CD-1 female mice with body weight 20–25 g (final weight at testing 20–30 g) were purchased from Charles River Laboratory (Wilmington, Mass., USA). The procedures were conducted in accordance with the appropriate regulations for the care and use of animals.

Methods

Experiments were carried out using a commercially available tail-flick analgesia meter (model TF-6 analgesia meter, Emdie Instrument Company, Maidens, Va., USA). The radiant heat source was set so that the control mice had a tail-flick latency of 2 to 4 seconds. A 10-second cutoff time was used as the maximum latency to avoid tissue damage. The tail flick latency of each mouse (a mean of two separate test results for each time point) was obtained at the 0 (immediately before dosing), 5, 15, 30 and 60 minute time points after injection of 4-s-[4-(propylsulfanyl)-1,2,5-thiadiazol-3-yl]-1-azatricyclo[3.3.1.1<3,7>]decane hydrochloride and/or morphine.

At ambient temperature, a temperature probe (Type T Thermocouple thermometer, BAT-10; Physitemp Inc., Clifton, N.J., USA) was inserted 1.5 cm into the rectum of each mouse to measure their core temperature and recorded at 0 (immediately before drug as a baseline control), 10, 25 and 55 minutes after injection of 4-s-[4-(propylsulfanyl)-1,2,5-thiadiazol-3-yl]-1-azatricyclo[3.3.1.1<3,7>]decane hydrochloride and/or morphine.

Observations of tremor, sedation, and salivation were made by close visual inspection of the mice at 5, 15, 30 and 60 minutes after injection of 4-s-[4-propylsulfanyl)-1,2,5-thiadiazol-3-yl]-1-azatricyclo[3.3.1.1<3,7>]decane hydrochloride. Tremor and sedation were scored as +(indicated visible tremor or sedation) or −(indicated non-visible tremor or sedation). Salivation was scored according to the following scale: 0, no sign of saliva within animal's mouth; 1, evidence of saliva in animal's mouth, but not on animal's muzzle; and 2, evidence of saliva in animal's mouth and on muzzle. No other muscarinic receptor mediated activities were observed.

4-s-[4-(propylsulfanyl)-1,2,5-thiadiazol-3-yl]-1-azatricyclo[3.3.1.1<3,7>]decane hydrochloride and morphine were injected subcutaneously (sc). Control animals received the corresponding vehicle(s) by the same route of administration.

Data Analysis

The percentage of maximum possible effect (%MPE) was calculated as follows:

%MPE=[(postdrug latency−predrug latency)÷(cutoff time−predrug latency)]×100%.

All results were expressed as mean±SEM. The response of 4-s-[4-(propylsulfanyl)-1,2,5-thiadiazol-3-yl]-1-azatricyclo[3.3.1.1<3,7>]decane hydrochloride or morphine with vehicle was compared with that of the combination of these two compounds for the corresponding dose. This comparison was carried out at the peak of antinociception (30 minutes). Student's T test (one tailed analysis) (Microsoft Excel 97, Microsoft Corporation, Redmond, Wash., USA) was used to analyse the statistical significance between the two groups. The value of p<0.05 was considered as statistically significant.

| Abbreviations | |
|---|---|
| BT | body temperature |
| ° C. | degrees Celsius |
| cm | centimeter |
| ED$_{50}$ | dose that produce a 50% effect |
| FM | formula mass |
| kg | kilogram |
| min | minute |

| Abbreviations | |
|---|---|
| mg | milligram |
| ml | milliliter |
| MPE | Maximum Possible Effect |
| n | number |
| NaCl | sodium chloride |
| sc | subcutaneous |
| SEM | standard error of the mean |
| % | percent |

2. Results 4-s-[4-(Propylsulfanyl)-1,2,5-thiadiazol-3-yl]-1-azatricyclo[3.3.1.1<3,7>]decane hydrochloride (0.03 mg/kg sc) and morphine (3 mg/kg sc).

4s-[4-(propylsulfanyl)-1,2,5-thiadiazol-3-yl]-1-azatricyclo[3.3.1.1<3,7>]decane hydrochloride (0.03 mg/kg sc) or morphine (3 mg/kg sc) alone produced modest antinociception (19% and 13% at 30 min, respectively). When a combination of these two compounds was tested, the antinociception was significantly enhanced (52%. P<0.05). The hypothermia produced by morphine was not significantly enhanced in the presence 4-s-[4-(propylsulfanyl)-1,2,5-thiadiazol-3-yl]-1-azatricyclo[3.3.1.1<3,7>]decane hydrochloride (p>0.05). Few other side effects were noted in this set of experiments.

4-s-[4-(propylsulfanyl)-1,2,5-thiadiazol-3-yl]-1-azatricyclo[3.3.1.1<3,7>]decane hydrochloride (0.03 mg/kg sc) and morphine (5.0 me/kg sc).

4-s-[4-(propylsulfanyl)-1,2,5-thiadiazol-3-yl]-1-azatricyclo[3.3.1.1<3,7>]decane hydrochloride (0.03 mg/kg sc) and morphine (5.0 mg/kg sc) produced modest antinociception (27% and 35% at 30 min, respectively). The antinociception produced by a combination of 4-s-[4-(propylsulfanyl)-1,2,5-thiadiazol-3-yl]-1-azatricyclo[3.3.1.1<3,7>]decane hydrochloride and morphine was increased significantly compared to that produced by either agent alone (97% at 30 min. p<0.001). The hypothermia produced by morphine was not significantly enhanced when a combination of 4-s-[4-(propylsulfanyl)-1,2,5-thiadiazol-3-yl]-1-azatricyclo[3.3.1.1<3,7>]decane hydrochloride and morphine was tested. Few other side effects were noted in this series of experiments.

4-s-[4-(propylsulfanyl)-1,2,5-thiadiazol-3-yl]-1-azatricyclo[3.3.1.1<3,7>]decane hydrochloride (0.05 mg/kg sc) and morphine (3 mg/kg sc).

4-s-[4-(propylsulfanyl)-1,2,5-thiadiazol-3-yl]-1-azatricyclo[3.3.1.1<3,7>]decane hydrochloride (0.05 mg/kg sc) or morphine (3 mg/kg sc) alone produced modest antinociception (38% and 25% at 30 min, respectively). The antinociception produced by a combination of 4-s-[4-(propylsulfanyl)-1,2,5-thiadiazol-3-yl]-1-azatricyclo[3.3.1.1<3,7>]decane hydrochloride and morphine was increased significantly compared to that produced by either agent alone (98%. P<0.001). In this series of experiments a combination of the two drugs produced greater hypothermia than that produced by either drug alone (p<0.001). Again few other side effects were noted.

3. Discussion 4-s-[4-(propylsulfanyl)-1,2,5-thiadiazol-3-yl]-1-azatricyclo[3.3.1.1>]decane hydrochloride is a potent antinociceptive agent in the mouse tail-flick test, being 300–1000 fold more potent than morphine. In contrast to other muscarinic agonists (Ellis et al., The Journal of Pharmacology and Experimental Therapeutics, 288(3), 1999), it exhibits a low incidence of muscarinic side effects at its ED$_{50}$ dose. The opiate analgesic morphine is widely used for the treatment of moderate to severe pain. Its use is limited by side effects such as addiction, sedation, constipation and pulmonary depression. In addition some pain states (e.g. neuropathic pain) can be refractive to morphine. In the present study a combination of combining 4-s-[4-(propylsulfanyl)-1,2,5-thiadiazol-3-yl]-1-azatricyclo[3.3.1.1<3,7>]decane hydrochloride and morphine yields significantly greater antinociception than either agent alone does. This enhanced antinociceptive activity may be useful in a clinical setting to either enhance the efficacy of either drug or to allow a lower dose to be used thus maintaining efficacy while lowering the side effect profile.

B. Potentiation of 4-s-[4-(propylsulfanyl)-1,2,5-thiadiazol-3-yl]-1-azatricyclo[3.3.1.1<3,7>]decanes hydrochloride Antinociception by NSAIDs in the Mouse Tail-flick Test In this series of mouse tail-flick experiments, 4-s-[4-(propylsulfanyl)-1,2,5-thiadiazol-3-yl]-1-azatricyclo[3.3.1.1<3,7>]decane hydrochloride was tested in combination with nonsteroidal anti-inflammatory drugs (NSAIDs). Other possible muscarinic agonist activities, such as tremor, sedation, salivation, and hypothermia were also observed.

1. Materials and Methods

Test Substances 4-s-[4-(propylsulfanyl)-1,2,5-thiadiazol-3-yl]-1-azatricyclo[3.3.1.1<3,7>]decane hydrochloride was dissolved in normal physiological saline (0.9% NaCl solution) for sc administration. The final dosing solution of 4-s-[4-(propylsulfanyl)-1,2,5-thiadiazol-3-yl]-1-azatricyclo[3.3.1.1<3,7>]decane hydrochloride was prepared so that the appropriate dose (0.03 mg/kg) was achieved with 10 ml/kg (body weight) of injected test compound solution.

Ibuprofen was purchased from Sigma Chemical Co. (I-1892; St. Louis, Mo., USA) and dissolved in ethyl alcohol (Aaper Alcohol and Chemical Co.) Subsequently, this solution was diluted in normal physiological saline (0.9% NaCl solution) so that the concentration of alcohol was 2.5% and that of ibuprofen was 5 mg/ml. At 10 ml/kg (body weight) volume of injection ip, the dose of ibuprofen was 50 mg/kg.

Acetaminophen was purchased from Sigma Chemical Co. (A-7085; St. Louis, Mo., USA) and dissolved in DMSO (Sigma Chemical Co., St. Louis, Mo., USA). Subsequently this solution was diluted in normal physiological saline (0.9% NaCl solution) so that the concentration of DMSO was 2% and that of acetaminophen was 6 mg/ml. At 10 ml/kg (body weight) volume of injection ip, the dose of acetaminophen was 60 mg/kg.

NS-398 was purchased from RBI (N-194; Sigma Chemical Co., St. Louis, Mo., USA) and dissolved in DMSO (Sigma Chemical Co., St. Louis, Mo., USA). Then this solution was diluted with normal physiological saline (0.9% NaCl solution) so that the concentration of DMSO was 2% and that of NS-398 0.05 mg/ml. At 10 ml/kg (body weight) volume of injection ip, the dose of NS-398 was 0.5 mg/kg.

Animals

CD-1 female mice with body weight 20–25 g (final weight at testing 20–30 g) were purchased from Charles River Laboratory (Wilmington, Mass., USA). The procedures were conducted in accordance with the appropriate regulations for the care and use of animals.

Methods

Experiments were carried out using a commercially available tail-flick analgesia meter (model TF-6 analgesia meter, Emdie Instrument Company, Maidens, Va., USA). The radiant heat source was set so that the control mice had a tail-flick latency of 2 to 4 seconds. A 10-second cutoff time was used as the maximum latency to avoid tissue damage. The tail flick latency of each mouse (a mean of two separate test results for each time point) was obtained at the 0 (immediately before dosing), 5, 15, 30 and 60 minute time points after injection of 4-s-[4-(propylsulfanyl)-1,2,5-thiadiazol-3-yl]-1-azatricyclo[3.3.1.1<3,7>]decane hydrochloride.

At ambient temperature, a temperature probe (Type T Thermocouple thermometer, BAT-10; Physitemp Inc., Clifton, N.J., USA) was inserted 1.5 cm into the rectum of each mouse to measure their core temperature and recorded at 0 (immediately before drug as a baseline control), 10, 25 and 55 minutes after injection of 4-s-[4-(propylsulfanyl)-1,2,5-thiadiazol-3-yl]-1-azatricyclo[3.3.1.1<3,7>]decane hydrochloride.

Observations of tremor, sedation, and salivation were made by close visual inspection of the mice at 5, 15, 30 and 60 minutes after injection of 4-s-[4-(propylsulfanyl)-1,2,5-thiadiazol-3-yl]-1-azatricyclo[3.3.1.1<3,7>]decane hydrochloride. Tremor and sedation were scored as +(indicated visible tremor or sedation) or −(indicated non-visible tremor or sedation). Salivation was scored according to the following scale: 0, no sign of saliva within animal's mouth; 1, evidence of saliva in animal's mouth, but not on animal's muzzle; and 2, evidence of saliva in animal's mouth and on muzzle. No other muscarinic receptor mediated activities were observed.

4-s-[4-(propylsulfanyl)-1,2,5-thiadiazol-3-yl]-1-azatricyclo[3.3.1.1<3,7>]decane hydrochloride and tested NSAIDs were injected subcutaneously (sc) or intraperitoneally (ip) respectively. Control animals received the corresponding vehicle(s) by the same route of administration.

Data Analysis

The percentage of maximum possible effect (%MPE) was calculated as follows:

$$\%MPE = [(\text{postdrug latency} - \text{predrug latency}) \div (\text{cutoff time} - \text{predrug latency})] \times 100\%.$$

All results were expressed as mean±SEM. The response of 4-s-[4-(propylsulfanyl)-1,2,5-thiadiazol-3-yl]-1-azatricyclo[3.3.1.1<3,7>]decane hydrochloride alone was compared to the response achieved with 4-s-[4-(propylsulfanyl)-1,2,5-thiadiazol-3-yl]-1-azatricyclo[3.3.1.1<3,7>]decane hydrochloride in combination with one of the NSAIDs. This comparison was carried out at the peak of antinociception (30 minutes). One tailed Student's T test (Microsoft Excel 97, Microsoft Corporation, Seattle, Wash., USA) was used to analysis the statistical significance between the two groups. The value of p<0.05 was considered as statistically significant.

| Abbreviations | |
| --- | --- |
| BT | body temperature |
| ° C. | degrees Celsius |
| cox | cyclooxygenase |
| DMSO | dimethyl sulfoxide |
| ED$_{50}$ | dose that produces effects in 50% of animals |
| FM | formula mass |
| ip | intraperitoneal |
| kg | kilogram |
| min | minute |
| mg | milligram |
| ml | milliliter |
| MPE | Maximum Possible Effect |

-continued

| Abbreviations | |
|---|---|
| n | number |
| NaCl | sodium chloride |
| NSAIDs | nonsteroidal anti-inflammatory drugs |
| sc | subcutaneous |
| SEM | standard error of the mean |
| % | percent |

2. Results

4s-[4-(propylsulfanyl)-1,2,5-thiadiazol-3-yl]-1-azatricyclo[3.3.1.1<3,7>]decane hydrochloride and Ibuprofen.

4-s-[4-(propylsulfanyl)-1,2,5-thiadiazol-3-yl]-1-azatricyclo[3.3.1.1<3,7>]decane hydrochloride (0.03 mg/kg sc) alone produced modest antinociception (29% at 30 min) whereas ibuprofen (50 mg/kg ip) was without antinociceptive effect. In the presence of ibuprofen the antinociception produced by 4-s-[4-(propylsulfanyl)-1,2,5-thiadiazol-3-yl]-1-azatricyclo[3.3.1.1<3,7>]decane hydrochloride was significantly enhanced (70%, $P<0.05$). The side effect profile of 4-s-[4-(propylsulfanyl)-1,2,5-thiadiazol-3-yl]-1-azatricyclo[3.3.1.1<3,7>]decane hydrochloride was unaltered in the presence of ibuprofen.

4-s-[4-(propylsulfanyl)-1,2,5-thiadiazol-3-yl]-1-azatricyclo[3.3.1.1<3,7>]decane hydrochloride and Acetaminophen.

4-s-[4-(propylsulfanyl)-1,2,5-thiadiazol-3-yl]-1-azatricyclo[3.3.1.1<3,7>]decane hydrochloride (0.03 mg/kg sc) alone produced modest antinociception (17% at 30 min) whereas acetaminophen (60 mg/kg ip) was without antinociceptive effect. In the presence of acetaminophen the antinociception produced by 4-s-[4-(propylsulfanyl)-1,2,5-thiadiazol-3-yl]-1-azatricyclo[3.3.1.1<3,7>]decane hydrochloride was significantly enhanced (47%, $P<0.05$). The side effect profile of 4-s-[4-(propylsulfanyl)-1,2,5-thiadiazol-3-yl]-1-azatricyclo[3.3.1.1<3,7>]decane hydrochloride was unaltered in the presence of acetaminophen 4-s-[4-(propylsulfanyl)-1,2,5-thiadiazol-3-yl]-1-azatricyclo[3.3.1.1<3.7>]decane hydrochloride and NS-398.

4-s-[4-(propylsulfanyl)-1,2,5-thiadiazol-3-yl]-1-azatricyclo[3.3.1.1<3,7>]decane hydrochloride (0.03 mg/kg sc) alone produced modest antinociception (35% at 30 min) whereas NS-398 (0.05 mg/kg ip) was without antinociceptive effect. In the presence of NS-398 the antinociception produced by 4-s-[4-(propylsulfanyl)-1,2,5-thiadiazol-3-yl]-1-azatricyclo[3.3.1.1<3,7>]decane hydrochloride was significantly enhanced (79%, $P<0.05$). The side effect profile of 4-s-[4-(propylsulfanyl)-1,2,5-thiadiazol-3-yl]-1-azatricyclo[3.3.1.1<3,7>]decane hydrochloride was unaltered in the presence of NS-398.

3. Discussion

The data from these experiments show that NSAIDs, such as ibuprofen, acetaminophen and NS-398 (a selective COX-2 inhibitor) are able to potentiate the antinociception of 4s-[4-(propylsulfanyl)-1,2,5-thiadiazol-3-yl]-1-azatricyclo[3.3.1.1<3,7>]decane hydrochloride.

Unlike muscarinic agents NSAID's, which have limited efficacy in moderate to severe pain states, do not show activity in the mouse tail flick test. In the present study the ability of several NSAID's, namely acetaminophen, the non-selective COX inhibitor ibuprofen and the COX-2 selective inhibitor NS-398 to potentiate the antinociception produced by 4-s-[4-(propylsulfanyl)-1,2,5-thiadiazol-3-yl]-1-azatricyclo[3.3.1.1<3,7>]decane hydrochloride was tested. Each of these NSAID's, despite having no activity themselves, potentiated the antinociception produced by 4-s-[4-(propylsulfanyl)-1,2,5-thiadiazol-3-yl]-1-azatricyclo[3.3.1.1<3,7>]decane hydrochloride. Despite the increased antinociception, the nominal side effects produced by 4-s-[4-(propylsulfanyl)-1,2,5-thiadiazol-3-yl]-1-azatricyclo[3.3.1.1<3,7>]decane hydrochloride were not increased by the NSAID's.

This data argues that a combination of 4-s-[4-(propylsulfanyl)-1,2,5-thiadiazol-3-yl]-1-azatricyclo[3.3.1.1<3,7>]decane hydrochloride (or other muscarinic agonists) with NSAIDs may provide a real benefit in the treatment of moderate to severe pain.

We claim:

1. A pharmaceutical composition comprising 4-s-[4-(propylsulfanyl)-1,2,5-thiadiazol-3-yl]-1-azatricyclo[3.3.1.1<3,7>]decane hydrochloride and one or more additional analgesics, wherein the additional analgesic is a nonsteroidal anti-inflammatory drug or morphine, wherein the composition produces a synergistic or super-additive effect.

2. The composition according to claim 1 further comprising a pharmaceutically acceptable carrier.

3. The composition according to claim 1 wherein the additional analgesic is morphine.

4. The composition according to claim 1 wherein the additional analgesic is a non-steroidal anti-inflammatory drug.

5. The composition according to claim 4 wherein the non-steroid anti-inflammatory drug is selected from the group of acetaminophen, ibuprofen, celecoxib and rofecoxib.

* * * * *